United States Patent [19]
Cyrlin

[11] Patent Number: 5,352,702
[45] Date of Patent: Oct. 4, 1994

[54] METHOD FOR TREATING GLAUCOMA

[76] Inventor: Marshall N. Cyrlin, 6200 Northfield Rd., West Bloomfield, Mich. 48322

[21] Appl. No.: 13,563

[22] Filed: Feb. 4, 1993

[51] Int. Cl.$^5$ ............................................. A61K 31/19
[52] U.S. Cl. ................................... 514/571; 514/913
[58] Field of Search ............................... 514/571, 913

[56] References Cited

U.S. PATENT DOCUMENTS 3,255,241  6/1966  Schultz et al. ..................... 260/516
4,757,089  7/1988  Epstein ................................ 514/571

OTHER PUBLICATIONS

Chemical Abstract 117 (19):18 4817 K (1992), Liang et al.
Edecrin Product Sheet, Merck & Co., Inc., Oct. 1985.
Investigative Opthalmology & Visual Science, Mar. 15, 1991, vol. 32, No. 4, Abstract 992-45, Association for Research in Vision & Opthalmology.
American Journal of Opthalmology, vol. 66, Jul.-Dec., 1968 pp. 680-683, Jose D. Peczon, M.D. & W. Morton Grant, M.D.

*Primary Examiner*—Zohreh Fay
*Attorney, Agent, or Firm*—Basile and Hanlon

[57] ABSTRACT

A method for treating glaucoma in an eye of a human patient is disclosed. The method comprises the step of chronically, orally administering to the patient an unsaturated ketone derivative of an aryloxyacetic acid in an amount sufficient to safely and effectively lower intraocular pressure in the human eye. The unsaturated ketone derivative is selected from the group consisting of ethacrynic acid, an analog of ethacrynic acid, an ester derivative of ethacrynic acid, an ester derivative of an ethacrynic acid analog, an amide derivative of ethacrynic acid, an amide derivative of an ethacrynic acid analog, a pharmaceutically acceptable salt of ethacrynic acid, a pharmaceutically acceptable salt of an ethacrynic acid analog, a pharmaceutically acceptable salt of the ester derivative, a pharmaceutically acceptable salt of the amide derivative, and mixtures thereof. The amount administered is preferably between about 50 mg and about 75 mg two times per day.

18 Claims, 19 Drawing Sheets

METHOD FOR TREATING GLAUCOMA

BACKGROUND OF THE INVENTION

The present invention relates generally to a method for treating glaucoma, and more particularly to such a method which uses chronic oral administration of ethacrynic acid or an analog thereof in order to safely and effectively lower intraocular pressure in the human eye.

Glaucoma is a condition of the eye characterized by elevated intraocular pressure (for adults, any pressure above about 21 mm Hg). It is a chronic, blinding disease affecting millions worldwide, and is currently treated with a number of medications with varying degrees of safety and efficacy. Thus, since this is such a serious condition, researchers are continually attempting to develop treatments which could relieve or possibly cure the condition.

In 1968, Drs. Peczon and Grant explored the use of diuretic drugs for treating glaucoma with the aim of determining whether they affect the formation of aqueous humor. The drugs tested, in acute dosages, were ethacrynic acid, chlormerodrin, bendroflumethiazide, furosemide, and triamterene, these drugs being five chemically and pharmacologically different types. The tests were compared to tests of acetazolamide, a carbonic anhydrase inhibitor having a known effect on intraocular pressure in glaucomatous patients when administered acutely. The conclusions drawn from the tests indicated that, in patients with open angle glaucoma, no consistent reduction of ocular pressure was induced by ethacrynic acid, chlormerodrin, bendroflumethiazide or triamterene administered orally, and only slight reduction by furosemide, distinctly less than by acetazolamide. In conclusion, the report stated that none of various categories of diuretic agents had yet been found to the interfere with aqueous formation or to reduce ocular pressure as effectively as the carbonic anhydrase inhibitors and the hypertonic osmotic agents.

In U.S. Pat. No. 4,757,089 issued to Epstein, a method of increasing aqueous humor outflow is disclosed. The method comprises topically administering to the eye a compound containing one or more groups capable of reacting with sulfhydryl groups in the trabecular meshwork of the eye. A further embodiment comprises the microinjection of such a compound into the trabecular meshwork. The preferred compound is ethacrynic acid. Although the invention appears to provide effective, non-surgical treatment of glaucoma, the topical administration of ethacrynic acid to the eye may produce medically unacceptable side effects.

Topical ethacrynic acid mixed with cysteine drops has also been tested. The results showed a lowering in intraocular pressure in rabbits and cynomolgus monkeys when combined with n-acetyl cysteine pre-treatment to reduce corneal toxicity.

Thus, it is an object of the present invention to provide a method for treating glaucoma which is non-surgical, will safely and effectively lower the intraocular pressure of the eye without use of a masking agent, without medically unacceptable side effects, and can be self-administered by the patient under periodic medical supervision. It is a further object of the present invention to advantageously provide such a method which may also have a long term effect on lowering intraocular pressure. It is yet a further object of the present invention to provide such a method which may also be additive in effect, or enhance the effect of intraocular pressure lowering when administered with other agents.

SUMMARY OF THE INVENTION

The present invention addresses and solves all the problems enumerated above. The present invention comprises a method for treating glaucoma in an eye of a human patient. The method comprises the step of chronically, orally administering to the patient an unsaturated ketone derivative of an aryloxyacetic acid in an amount sufficient to safely and effectively lower intraocular pressure in the human eye. The unsaturated ketone derivative is selected from the group consisting of ethacrynic acid, an analog of ethacrynic acid, an ester derivative of ethacrynic acid, an ester derivative of an ethacrynic acid analog, an amide derivative of ethacrynic acid, an amide derivative of an ethacrynic acid analog, a pharmaceutically acceptable salt of ethacrynic acid, a pharmaceutically acceptable salt of an ethacrynic acid analog, a pharmaceutically acceptable salt of the ester derivative, a pharmaceutically acceptable salt of the amide derivative, and mixtures thereof. The amount administered is preferably between about 50 mg and about 75 mg two times per day.

BRIEF DESCRIPTION OF THE DRAWINGS

Other objects, features and advantages of the present invention will become apparent by reference to the following detailed description and drawings, in which.

DETAILED DESCRIPTION OF THE PREFERRED EMBODIMENTS

Figure 1:
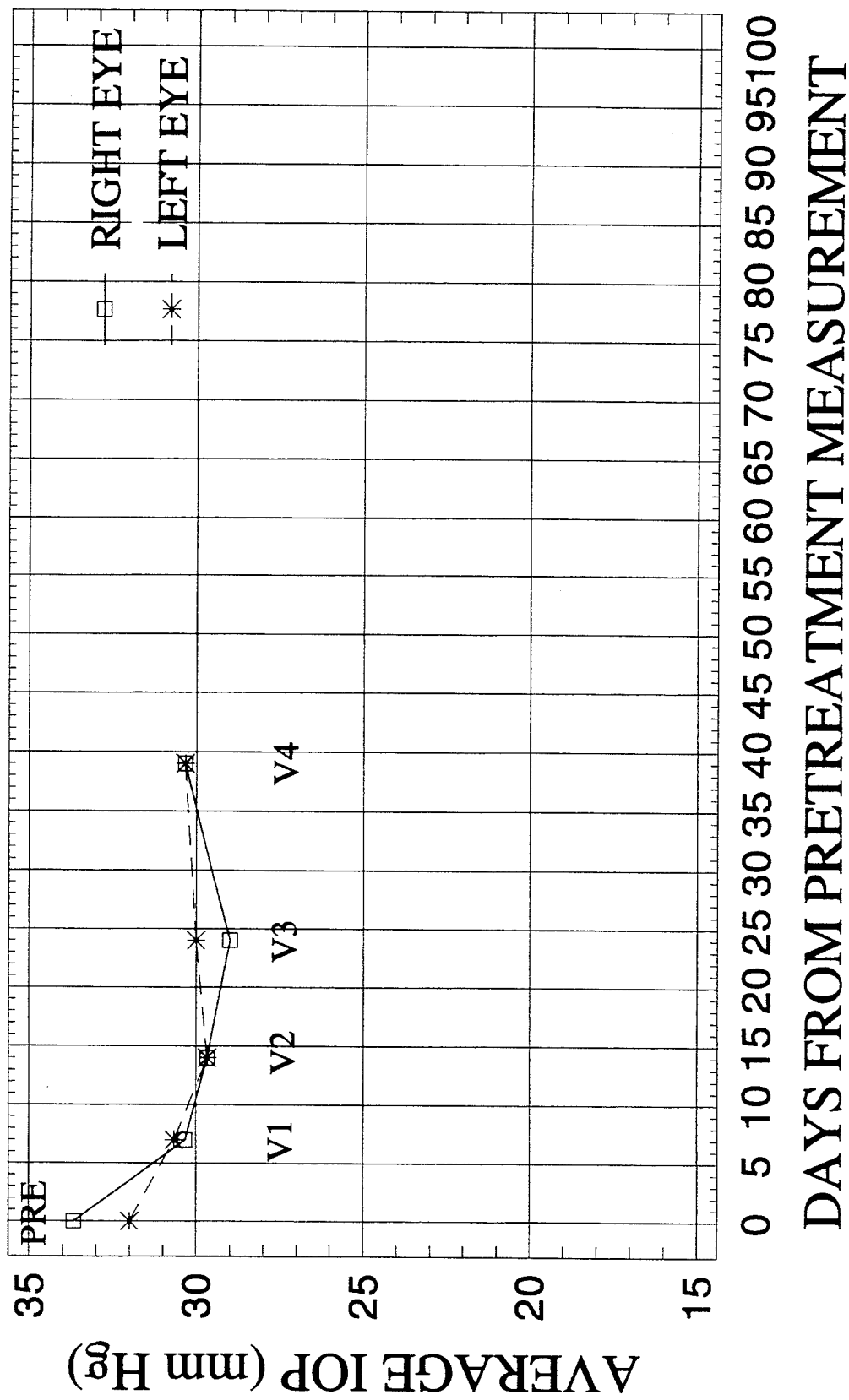
FIG. 1 is a graph showing the average intraocular pressures (IOP) plotted against days of treatment for the first patient treated according to the inventive method.
Figure 2:
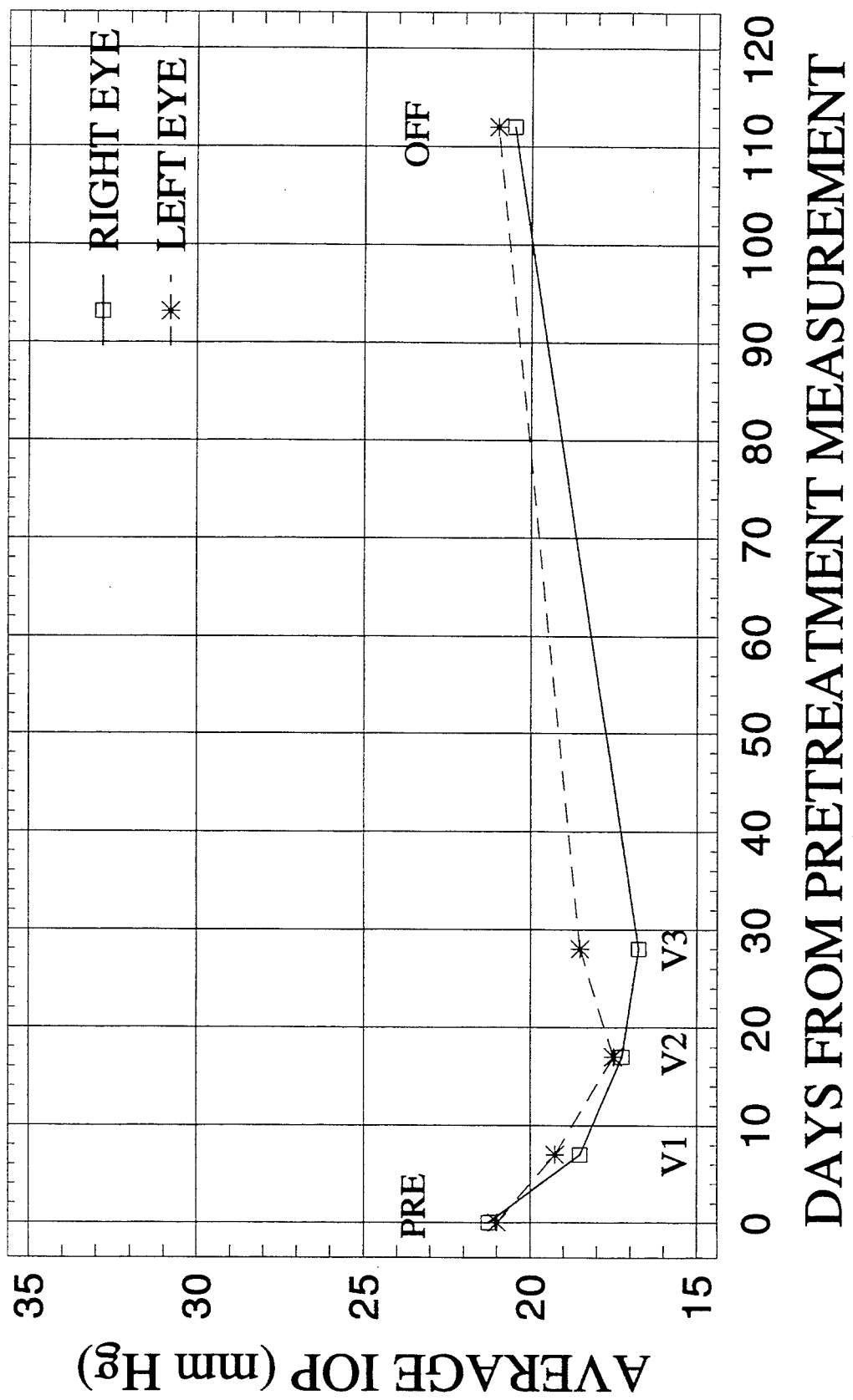
FIG. 2 is a graph showing the average intraocular pressures (IOP) plotted against days of treatment for the second patient treated according to the inventive method.
Figure 3:
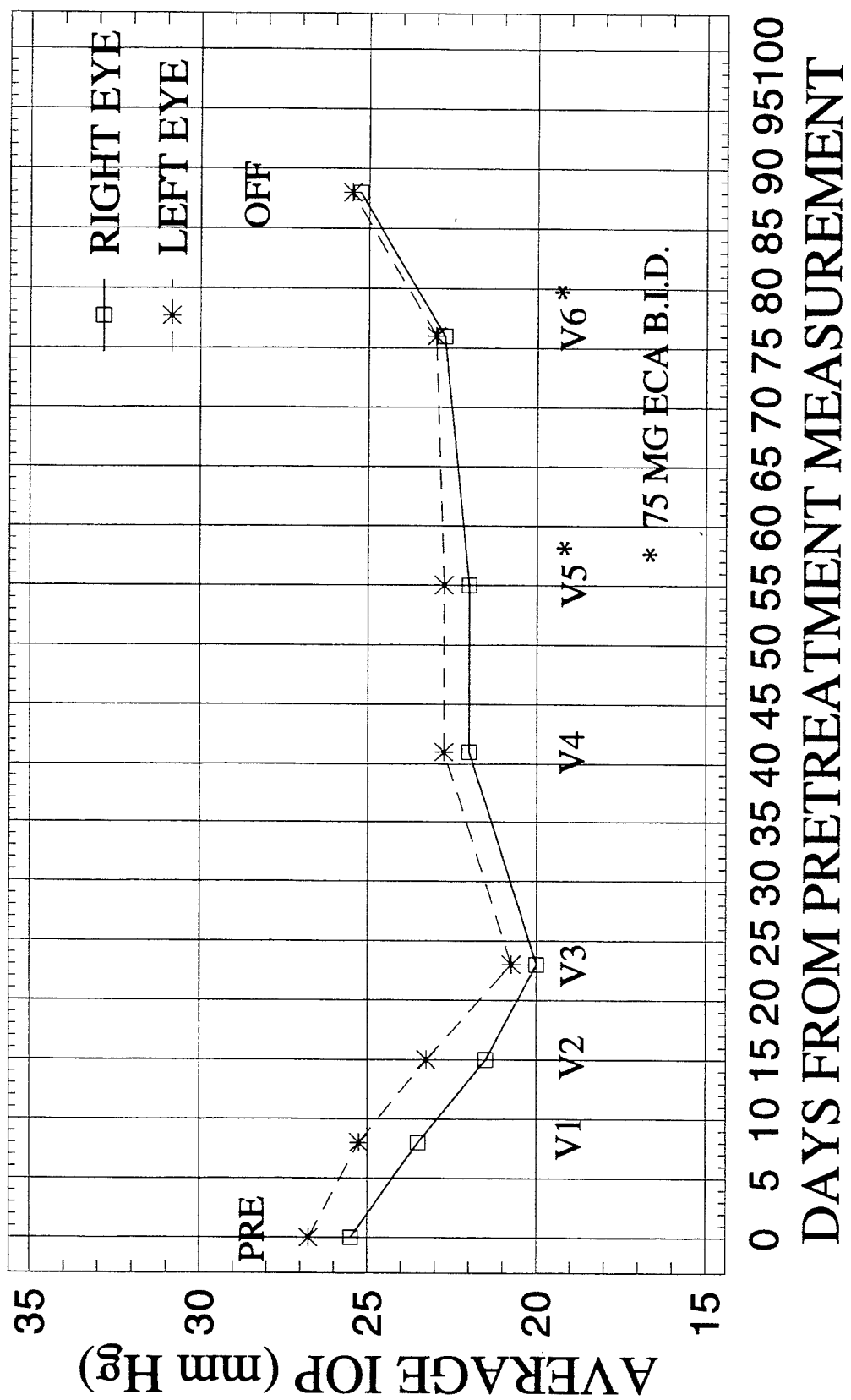
FIG. 3 is a graph showing the average intraocular pressures (IOP) plotted against days of treatment for the third patient treated according to the inventive method.
Figure 4:
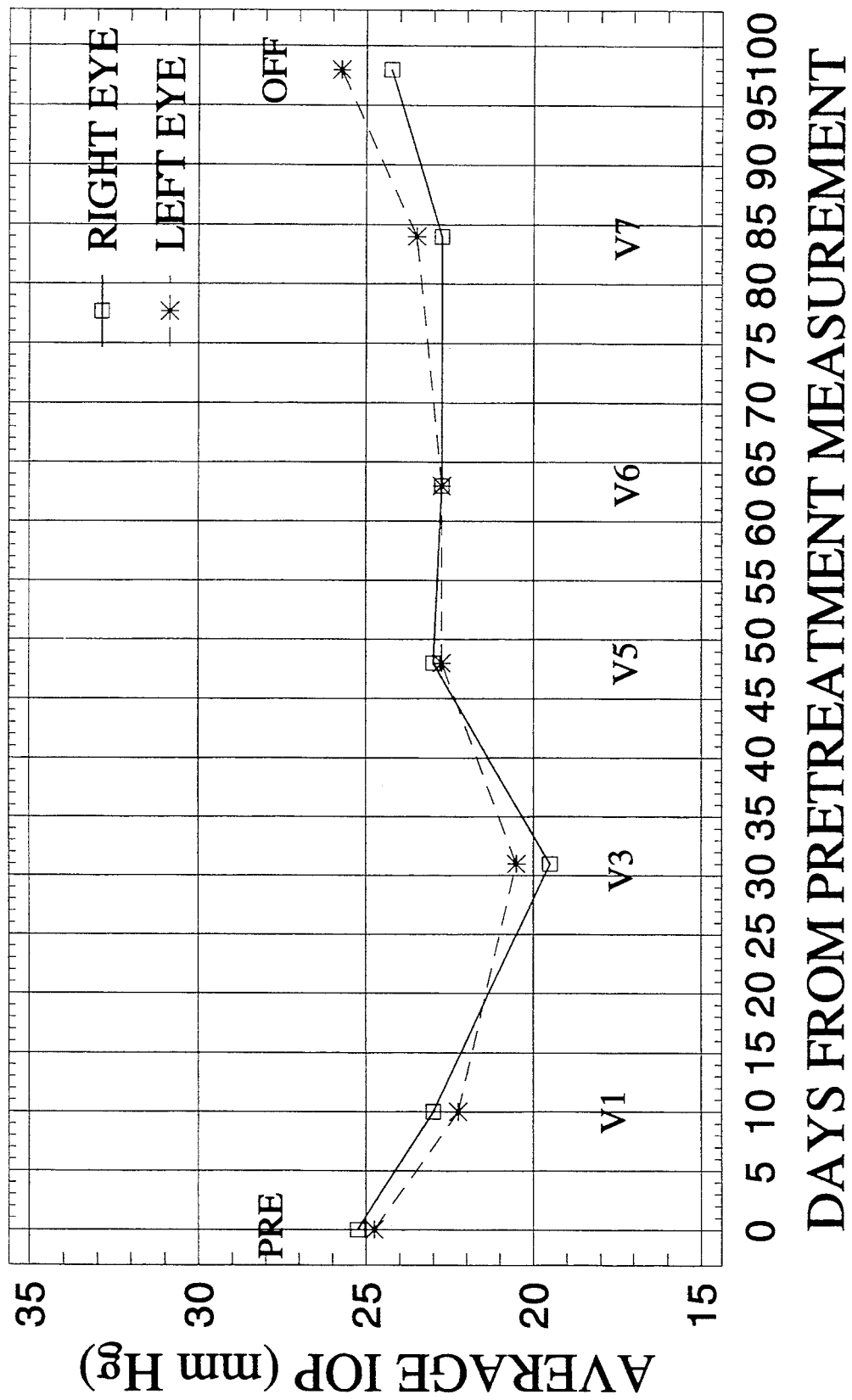
FIG. 4 is a graph showing the average intraocular pressures (IOP) plotted against days of treatment for the fourth patient treated according to the inventive method.

The present invention comprises a method for treating glaucoma in an eye of a human patient. The method comprises the step of chronically, orally administering to the patient an unsaturated ketone derivative of an aryloxyacetic acid in an amount sufficient to safely and effectively lower intraocular pressure in the human eye. The unsaturated ketone derivative is selected from the group consisting of ethacrynic acid, an analog of ethacrynic acid, an ester derivative of ethacrynic acid, an ester derivative of an ethacrynic acid analog, an amide derivative of ethacrynic acid, an amide derivative of an ethacrynic acid analog, a pharmaceutically acceptable salt of ethacrynic acid, a pharmaceutically acceptable salt of an ethacrynic acid analog, a pharmaceutically acceptable salt of the ester derivative, a pharmaceutically acceptable salt of the amide derivative, and mixtures thereof.

Ethacrynic acid is an unsaturated ketone derivative of an aryloxyacetic acid. It is designated chemically as [2,3-dichloro-4-(2-methylene-1-oxobutyl) phenoxy]acetic acids. Its structural formula is:

Ethacrynic acid is commercially available from Merck, Sharp & Dohme under the trademarks EDECRIN and SODIUM EDECRIN and is described in U.S. Pat. No. 3,255,241, which is hereby incorporated by reference. Any suitable analogs described in U.S. Pat. No. 3,255,241 can also be used in the present invention.

The unsaturated ketone derivative is of the general formula:

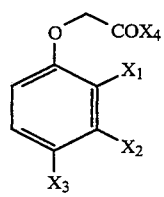

In the preferred embodiment, each $X_1$ and $X_2$, independently, is H, Cl, or $CH_3$, or $X_1$ and $X_2$ together form a phenyl ring; $X_3$ is one of chloropropanyl, tosyl or mesyl; and $X_4$ is one of hydroxy, amino or alkoxy.

In the preferred embodiment, ethacrynic acid is used. Some preferred embodiments of ethacrynic acid analogs include, but are not limited to, the following compounds:

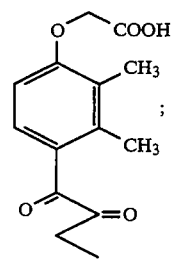

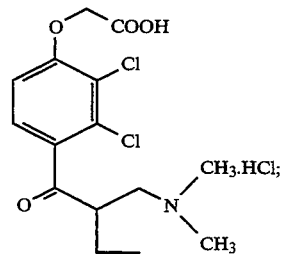

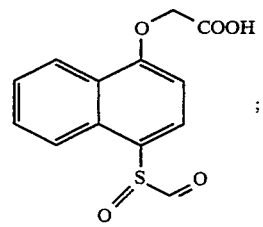

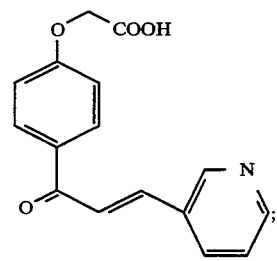

and

-continued

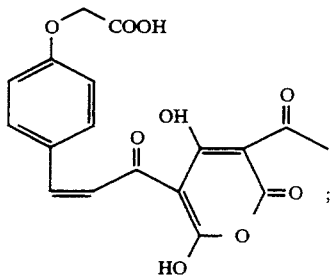

It was fortuitously demonstrated that the chronic oral administration of the inventive medication had an effect different from that when given acutely. Unlike most medications, which either have some effect when administered acutely, or none at all notwithstanding the amount (i.e. chronically administering an ineffective drug generally will continue to be ineffective), it was found that the medication used in the inventive method did indeed affect intraocular pressure upon chronic exposure to the tissue. Further, most medications upon being discontinued will cease to have any effect. However, that used in the inventive method appears to maintain a lasting effect.

Without being bound to any theory, it is believed that the compounds disclosed in the inventive method contain chemical groups which are capable of reacting with the sulfhydryl groups of the trabecular meshwork to increase aqueous humor outflow and decrease intraocular pressure. The reaction with the sulfhydryl groups takes place in a manner which will not cause an amount of swelling of the cells of the trabecular meshwork which could decrease outflow, particularly the inner wall endothelial cells of Schlemm's canal. Suitable sulfhydryl groups include, but are not limited to C≡C, C=O, sulfhydryl, alkyl (preferably methyl or ethyl) and aryl (phenyl) substituted with a good leaving group, for example halogen, tosyl or mesyl. Preferably, in the case of substituted alkyl groups, substitution is primary, rather than secondary or tertiary, for greater reactivity. Thus, in a preferred embodiment of the compound in the inventive method, $X_3$ is a sulfhydryl reactive organic group, as described above.

In the present method, the preferred administered amount varies between about 50 mg and about 75 mg two times per day, or between about 100 mg and about 150 mg daily. It is to be understood that the present amounts are approximate, and that the present method encompasses any administration amounts which will achieve the inventive results. It is to be further understood that "safely and effectively" read in conjunction with the present disclosure means that the inventive method may lower intraocular pressure, substantially without clinically unacceptable side effects. These side effects may include electrolyte imbalance, elevated levels of serum uric acid, glucose, and blood urea nitrogen.

Without being bound to any theory, the clinical response of certain patients to treatment according to the inventive method appears to indicate a long term lowering of intraocular pressure, even after discontinuing the medications. This would seem to suggest that the treatment has an effect on the cellular structure of the eye. As it also clinically appears that the treatment has an increasing effect with time, it is believed that the method of the present invention may lead to a lasting or semi-lasting lowering of intraocular pressure in the human eye, even after discontinuing the inventive medication, thereby giving a patient long term relief from glaucoma. An advantage of the present, orally administered method over topical administration or microinjection is that one does not risk corneal edema which can be caused by interaction between sulfhydryl reactive groups of the therapeutic compounds and the sulfhydryl groups in the corneal cells.

The present inventor conducted an initial study in which a dosage of 50 mg of ethacrynic acid was administered every 12 hours, for a minimum of three weeks, to 12 chronic glaucoma patients uncontrolled on a variety of standard medications. Morning diurnal intraocular pressure (IOP) and blood pressure measurements were obtained on a weekly basis. All persons studied showed at minimum some effect, in that there was some lowering of the intraocular pressure during treatment by the inventive method.

Twelve patients with open angle glaucoma entered into this study. The patients ranged in age from 39 to 80 years of age with an average age of 66 years. There was a past ocular history of bilateral argon laser trabeculoplasty in four patients, unilateral argon laser trabeculoplasty in two, trabeculectomy in one and bilateral argon laser iridectomy in one patient. Ocular medications included beta blockers, miotics and epinephrine in some patients. There was one patient on oral carbonic anhydrase inhibitor. Three patients were on no medication.

Treatment protocol consisted of a PRE study visit for baseline measurements followed by a minimum of three (V1, V2, V3) visits approximately one week apart. The patients self administered 50 mg of oral ethacrynic acid (ECA) every 12 hours beginning the evening of the PRE exam. They continued their prior ocular medication. All 12 patients completed the three visit schedule with the exception of one missing visit 2. One patient had the dose lowered to 50 mg ECA qd. Intraocular pressure measurements, on the same tonometer, by the same examiner, and blood pressure measurements by the same examiner were made at 8, 9, 10 and 11 am for each patient for PRE, V1, V2 and V3 except for two patients who were unable to be evaluated at 8 am. Blood samples were obtained for routine chemistries at PRE and V3.

Five patients remained on the same treatment regimen for an additional one to three visits (V4, V5, V6, V7) spaced one to three weeks apart with the exception of one patient whose dose was increased 75 mg ECA bid for the last two treatment visits. The same hourly protocol for measurement of IOP and blood pressure was followed.

A sub group of six patients were re-evaluated in the same fashion approximately one to two weeks following discontinuation of the ECA (OFF). One patient was discontinued (OFF1), retreated on the same dosage (REV1, REV2, REV3) and again discontinued (REOFF1, REOFF2).

Statistical analysis of paired data was performed by two tailed t test with statistical software. Calculations were based on the hourly IOP for each eye, for each subject for each visit. Mean percent change in outflow pressure was similarly calculated with ten mm Hg used as the estimated episcleral venous pressure. Average IOP for each patient, for each eye, for each visit and average IOP for both eyes, for each patient for each visit were calculated and plotted. Paired t test analysis was performed for blood chemistry results.

Mean intraocular pressures at each hour for the right eye is presented in Table 1 below, and for the left eye in Table 2 below.

TABLE 1

MEAN INTRAOCULAR PRESSURES

| Right Eye | Time | # patients Observed | Average | Standard Deviation |
|---|---|---|---|---|
| PRE | 8:00 AM | 10 | 24.60 | 2.32 |
| Visit 1 | 8:00 AM | 10 | 23.20 | 2.20 |
| Visit 2 | 8:00 AM | 9 | 22.67 | 2.55 |
| Visit 3 | 8:00 AM | 10 | 21.50 | 2.84 |
| PRE | 9:00 AM | 12 | 25.42 | 3.12 |
| Visit 1 | 9:00 AM | 12 | 23.17 | 3.74 |
| Visit 2 | 9:00 AM | 11 | 23.00 | 3.13 |
| Visit 3 | 9:00 AM | 12 | 22.75 | 3.33 |
| PRE | 10:00 AM | 12 | 25.58 | 3.70 |
| Visit 1 | 10:00 AM | 12 | 24.00 | 3.10 |
| Visit 2 | 10:00 AM | 11 | 23.18 | 3.66 |
| Visit 3 | 10:00 AM | 12 | 23.00 | 3.57 |
| PRE | 11:00 AM | 12 | 25.08 | 3.60 |
| Visit 1 | 11:00 AM | 12 | 23.33 | 2.50 |
| Visit 2 | 11:00 AM | 11 | 23.00 | 3.63 |
| Visit 3 | 11:00 AM | 12 | 22.92 | 3.68 |

TABLE 2

MEAN INTRAOCULAR PRESSURES

| Left Eye | Time | # patients Observed | Average | Standard Deviation |
|---|---|---|---|---|
| PRE | 8:00 AM | 10 | 24.30 | 3.71 |
| Visit 1 | 8:00 AM | 10 | 21.70 | 1.64 |
| Visit 2 | 8:00 AM | 9 | 21.67 | 2.24 |
| Visit 3 | 8:00 AM | 10 | 21.50 | 1.96 |
| PRE | 9:00 AM | 12 | 24.92 | 3.09 |
| Visit 1 | 9:00 AM | 12 | 22.75 | 3.60 |
| Visit 2 | 9:00 AM | 11 | 22.45 | 3.14 |
| Visit 3 | 9:00 AM | 12 | 22.25 | 3.39 |
| PRE | 10:00 AM | 12 | 25.08 | 3.45 |
| Visit 1 | 10:00 AM | 12 | 22.83 | 3.27 |
| Visit 2 | 10:00 AM | 11 | 22.64 | 3.91 |
| Visit 3 | 10:00 AM | 12 | 22.58 | 3.12 |
| PRE | 11:00 AM | 12 | 24.67 | 3.23 |
| Visit 1 | 11:00 AM | 12 | 23.25 | 3.14 |
| Visit 2 | 11:00 AM | 11 | 22.55 | 3.45 |
| Visit 3 | 11:00 AM | 12 | 22.75 | 3.25 |

Figure 13:
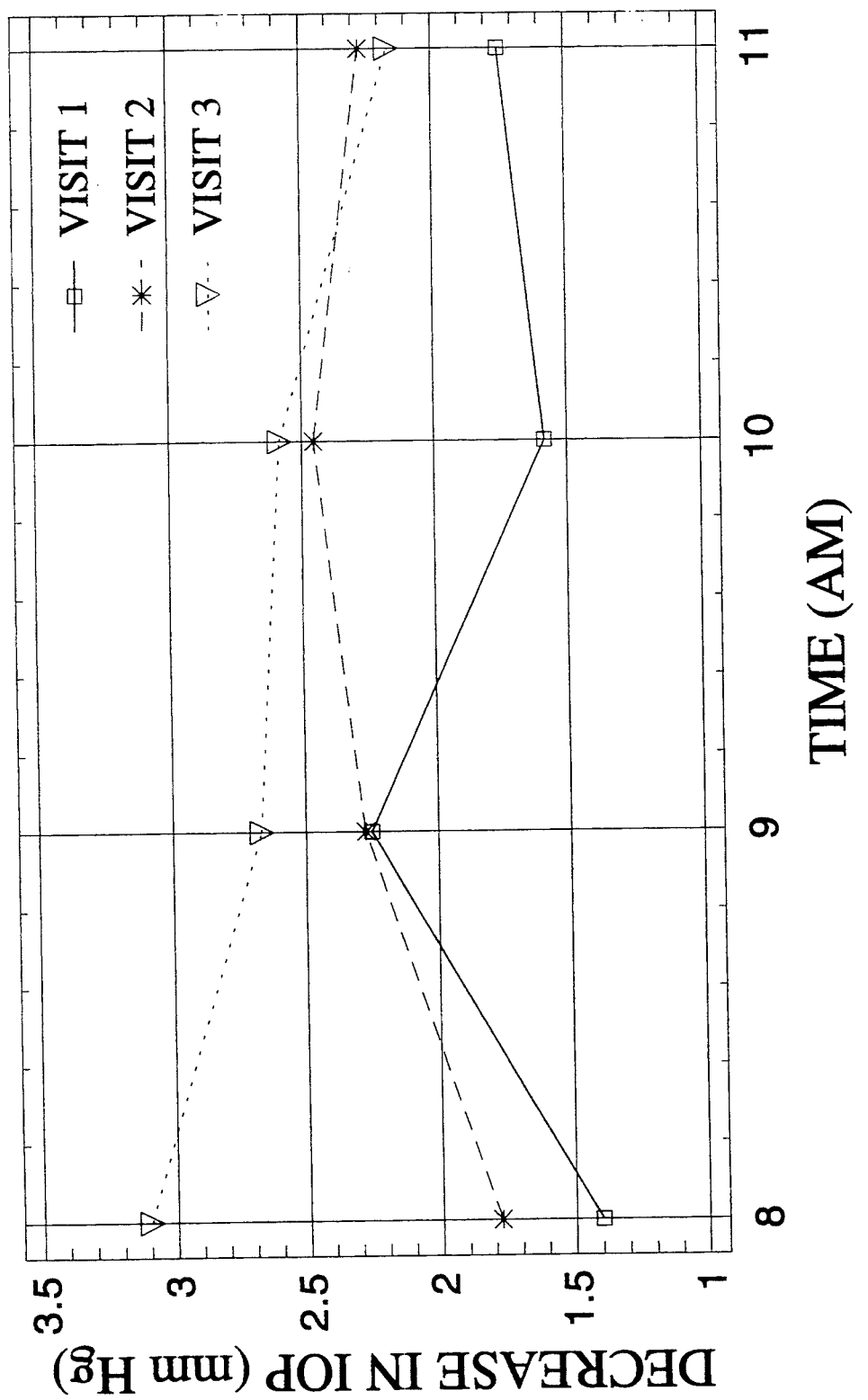
FIG. 13 is a graph showing the mean decrease in IOP for the right eye plotted against four hourly readings of patients treated according to the inventive method.
Figure 14:
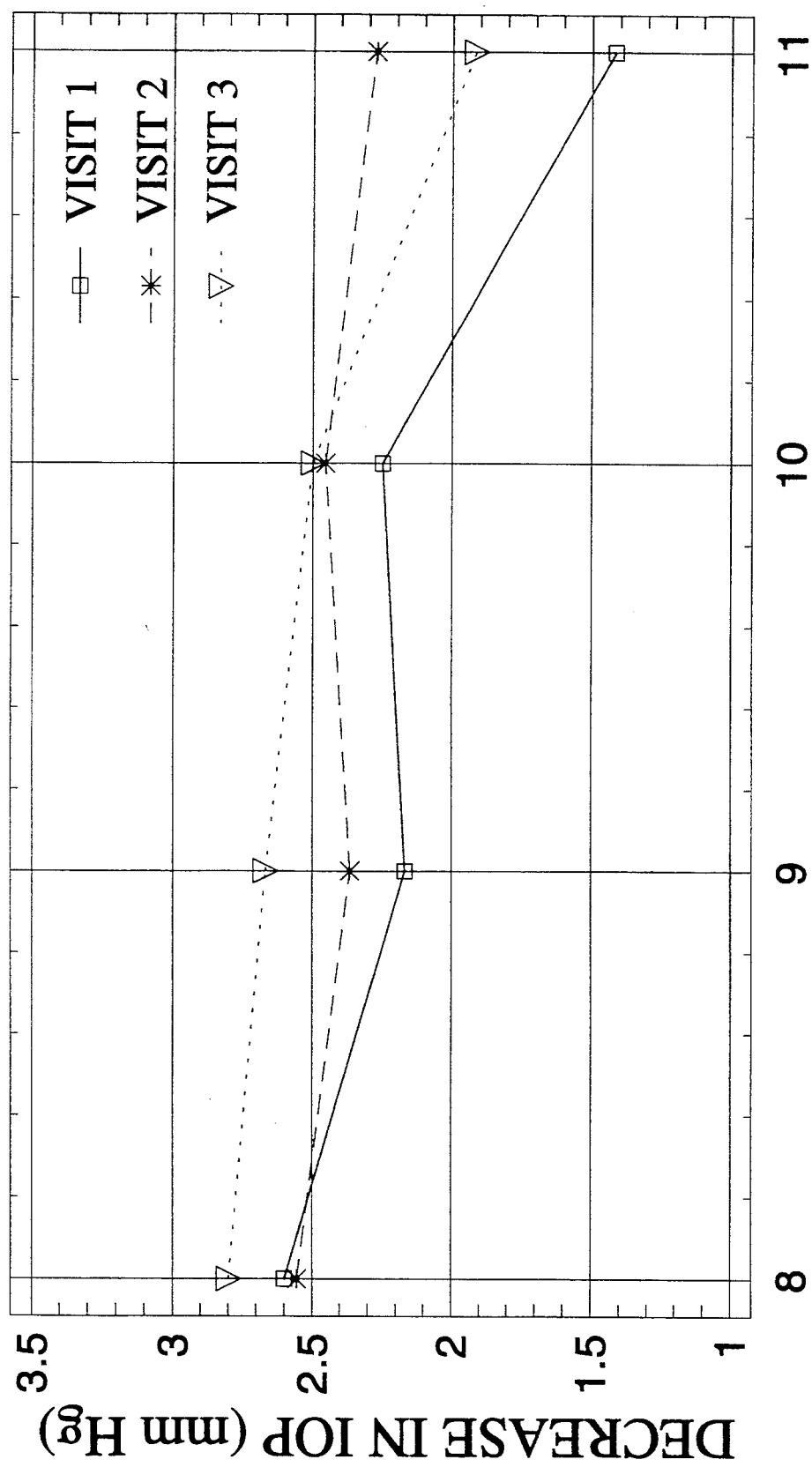
FIG. 14 is a graph showing the mean decrease in IOP for the left eye plotted against four hourly readings of patients treated according to the inventive method.

The mean decrease in IOP for the right eye is presented in Table 3 below, and for the left eye in Table 4 below. This mean decrease in IOP is also graphically depicted for the right eye in FIG. 13, and for the left eye in FIG. 14. The decrease in pressure was significant at P<0.01 for 19 of the 24 differences and was significant at P<0.05 for all measurements. The only significant changes found between the hourly differences for visit 1 and visit 2 or visit 1 and visit 3 were visit 1–visit 3 in the right eye at 8 am (P<0.014) and 10 am (P≦0.0203).

TABLE 3

MEAN DECREASE IN IOP

| Right Eye | Time | # patients Observed | Average | Standard Deviation | Sig p ≦ |
|---|---|---|---|---|---|
| Visit 1 | 8:00 AM | 10 | −1.40 | 1.35 | 0.0095 |
| Visit 2 | 8:00 AM | 9 | −1.78 | 2.17 | 0.0392 |
| Visit 3 | 8:00 AM | 10 | −3.10 | 2.64 | 0.0049 |
| Visit 1 | 9:00 AM | 12 | −2.25 | 1.60 | 0.0005 |
| Visit 2 | 9:00 AM | 11 | −2.27 | 1.42 | 0.0003 |
| Visit 3 | 9:00 AM | 12 | −2.67 | 2.23 | 0.0016 |
| Visit 1 | 10:00 AM | 12 | −1.58 | 1.38 | 0.0022 |
| Visit 2 | 10:00 AM | 11 | −2.45 | 2.30 | 0.0053 |
| Visit 3 | 10:00 AM | 12 | −2.58 | 2.11 | 0.0014 |
| Visit 1 | 11:00 AM | 12 | −1.75 | 1.60 | 0.0030 |
| Visit 2 | 11:00 AM | 11 | −2.27 | 1.85 | 0.0022 |
| Visit 3 | 11:00 AM | 12 | −2.17 | 2.37 | 0.0089 |

TABLE 4

MEAN DECREASE IN IOP

| Left Eye | Time | # patients Observed | Average | Standard Deviation | Sig p ≦ |
|---|---|---|---|---|---|
| Visit 1 | 8:00 AM | 10 | −2.60 | 3.10 | 0.0263 |
| Visit 2 | 8:00 AM | 9 | −2.56 | 3.09 | 0.0379 |
| Visit 3 | 8:00 AM | 10 | −2.80 | 3.01 | 0.0165 |
| Visit 1 | 9:00 AM | 12 | −2.17 | 1.34 | 0.0002 |
| Visit 2 | 9:00 AM | 11 | −2.36 | 1.29 | 0.0001 |
| Visit 3 | 9:00 AM | 12 | −2.67 | 1.87 | 0.0005 |
| Visit 1 | 10:00 AM | 12 | −2.25 | 1.48 | 0.0003 |
| Visit 2 | 10:00 AM | 11 | −2.45 | 1.63 | 0.0006 |
| Visit 3 | 10:00 AM | 12 | −2.50 | 1.78 | 0.0005 |
| Visit 1 | 11:00 AM | 12 | −1.42 | 2.02 | 0.0335 |
| Visit 2 | 11:00 AM | 11 | −2.27 | 1.19 | 0.0001 |
| Visit 3 | 11:00 AM | 12 | −1.92 | 1.56 | 0.0014 |

Figure 15:
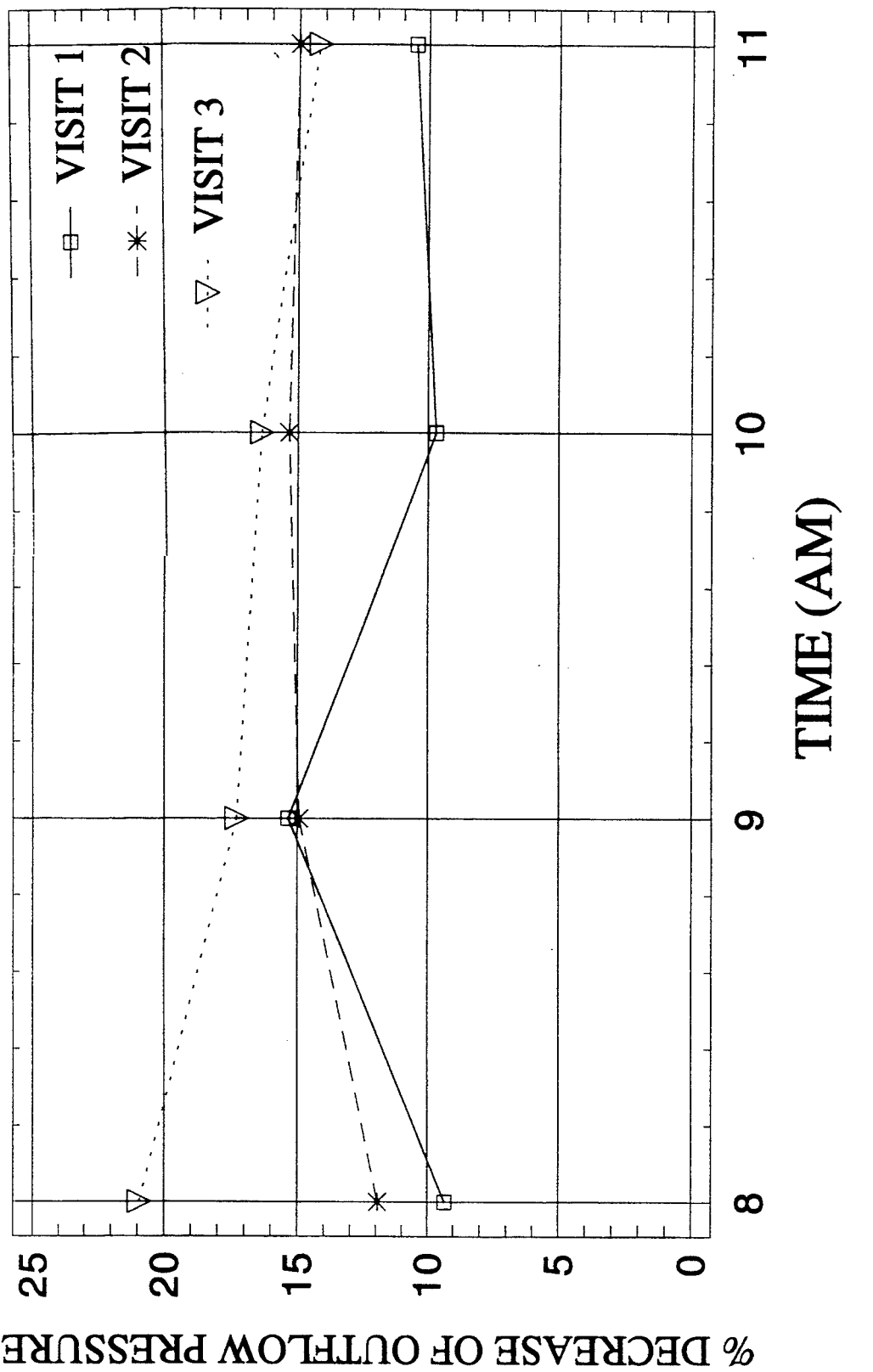
FIG. 15 is a graph showing the mean percent decrease in outflow pressure for the right eye plotted against four hourly readings for patients treated according to the inventive method.
Figure 16:
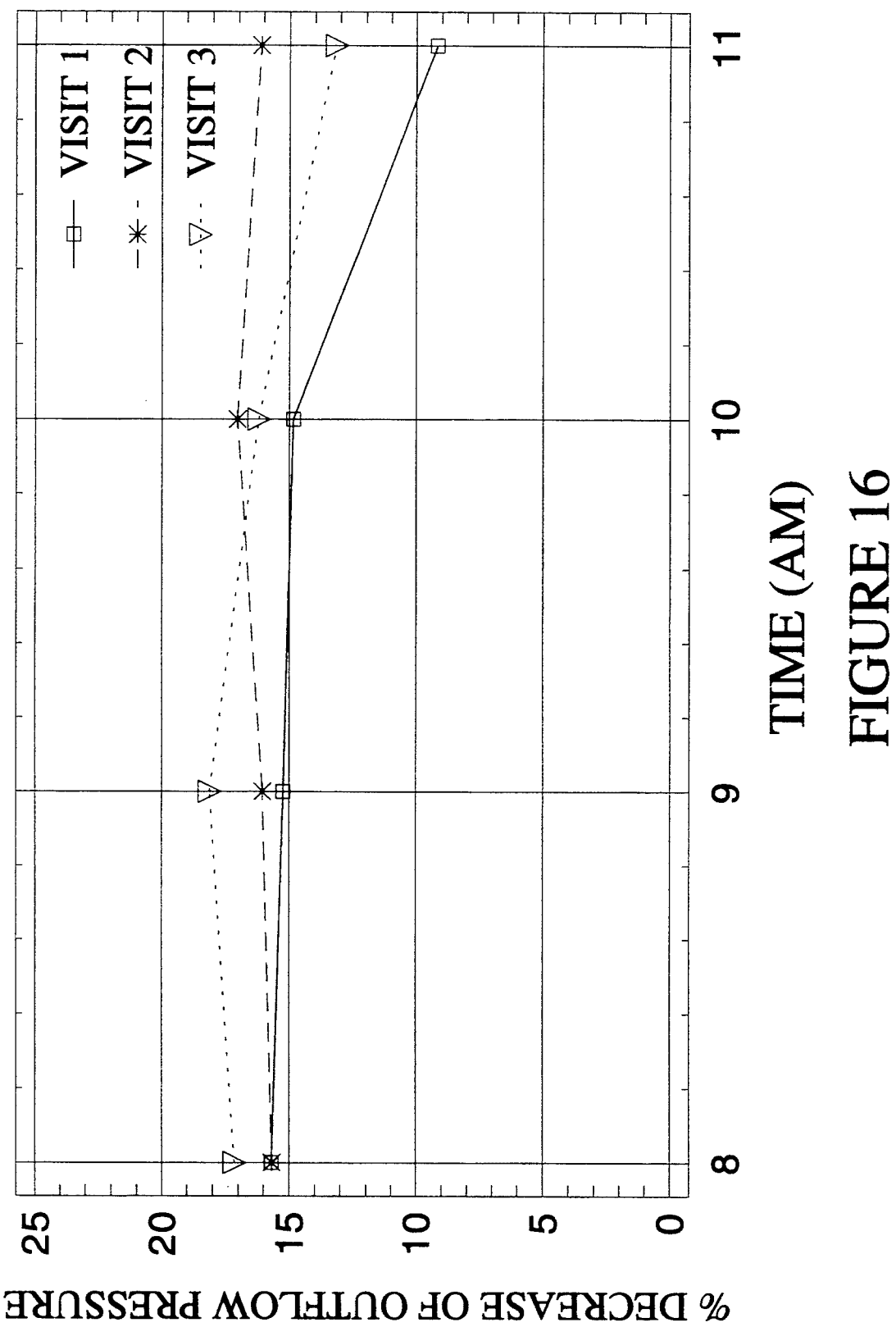
FIG. 16 is a graph showing the mean percent decrease in outflow pressure for the left eye plotted against four hourly readings for patients treated according to the inventive method.

The mean percent decrease in outflow pressure from PRE for V1, V2 and V3 for each hour for the right eye is shown in Table 5 below, and for the left eye as shown in Table 6 below. This mean percent decrease in outflow pressure is also graphically depicted for the right eye in FIG. 15, and for the left eye in FIG. 16. The percent decrease in outflow pressure was significant at P<0.01 for 21 of the 24 differences and was significant at P<0.05 for all measurements. The only significant changes found between the hourly differences for V1 and V2 or V1 and V3 were V1–V3 for the right eye at 8 am (P<0.011) and 10 am (P≦0.018).

TABLE 5

MEAN % DECREASE OUTFLOW PRESSURE

| Right Eye | Time | # patients Observed | Average | Standard Deviation | Sig p ≦ |
|---|---|---|---|---|---|
| Visit 1 | 8:00 AM | 10 | −9.33 | 8.57 | 0.0073 |
| Visit 2 | 8:00 AM | 9 | −11.94 | 13.80 | 0.0319 |
| Visit 3 | 8:00 AM | 10 | −20.93 | 16.82 | 0.0034 |
| Visit 1 | 9:00 AM | 12 | −15.34 | 12.02 | 0.0010 |
| Visit 2 | 9:00 AM | 11 | −14.94 | 9.63 | 0.0004 |
| Visit 3 | 9:00 AM | 12 | −17.29 | 14.37 | 0.0016 |
| Visit 1 | 10:00 AM | 12 | −9.68 | 8.56 | 0.0024 |
| Visit 2 | 10:00 AM | 11 | −15.33 | 15.97 | 0.0098 |
| Visit 3 | 10:00 AM | 12 | −16.37 | 14.15 | 0.0021 |
| Visit 1 | 11:00 AM | 12 | −10.49 | 7.95 | 0.0008 |
| Visit 2 | 11:00 AM | 11 | −14.97 | 14.76 | 0.0072 |
| Visit 3 | 11:00 AM | 12 | −14.21 | 17.90 | 0.0189 |

TABLE 6

MEAN % DECREASE OUTFLOW PRESSURE

| Left Eye | Time | # patients Observed | Average | Standard Deviation | Sig p ≦ |
|---|---|---|---|---|---|
| Visit 1 | 8:00 AM | 10 | −15.69 | 12.42 | 0.0031 |
| Visit 2 | 8:00 AM | 9 | −15.67 | 15.35 | 0.0155 |
| Visit 3 | 8:00 AM | 10 | −17.16 | 14.63 | 0.0049 |
| Visit 1 | 9:00 AM | 12 | −15.24 | 8.09 | 0.0000 |
| Visit 2 | 9:00 AM | 11 | −16.04 | 7.25 | 0.0000 |
| Visit 3 | 9:00 AM | 12 | −18.11 | 11.48 | 0.0002 |
| Visit 1 | 10:00 AM | 12 | −14.84 | 10.01 | 0.0003 |
| Visit 2 | 10:00 AM | 11 | −17.03 | 12.85 | 0.0013 |
| Visit 3 | 10:00 AM | 12 | −16.20 | 10.59 | 0.0003 |
| Visit 1 | 11:00 AM | 12 | −9.17 | 12.38 | 0.0262 |
| Visit 2 | 11:00 AM | 11 | −16.11 | 9.20 | 0.0002 |

TABLE 6-continued

| Left Eye | Time | # patients Observed | Average | Standard Deviation | Sig p ≦ |
|---|---|---|---|---|---|
| | | MEAN % DECREASE OUTFLOW PRESSURE | | | |
| Visit 3 | 11:00 AM | 12 | −13.16 | 9.98 | 0.0008 |

Figure 11:
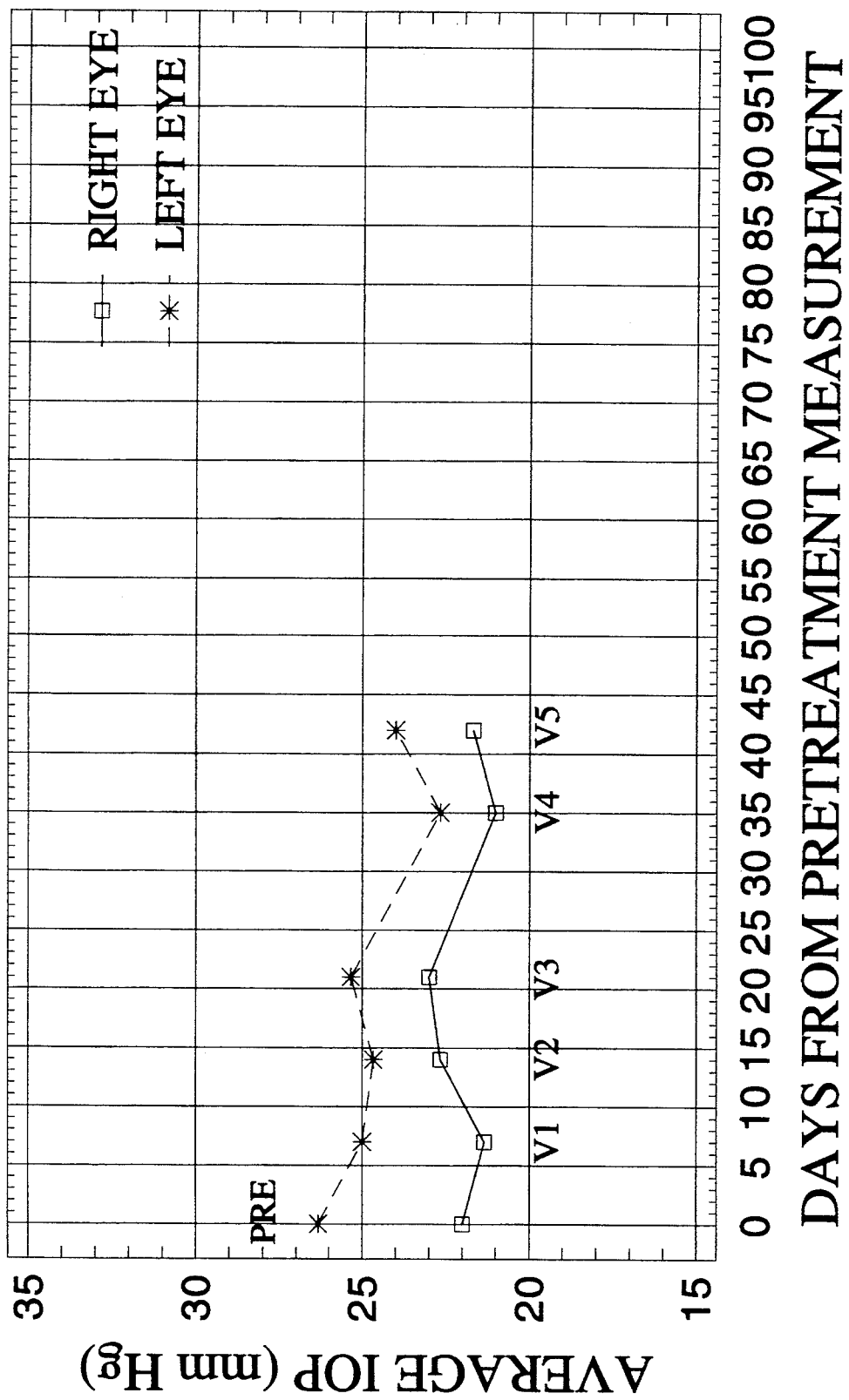
FIG. 11 is a graph showing the average intraocular pressures (IOP) plotted against days of treatment for the eleventh patient treated according to the inventive method.
Figure 12:
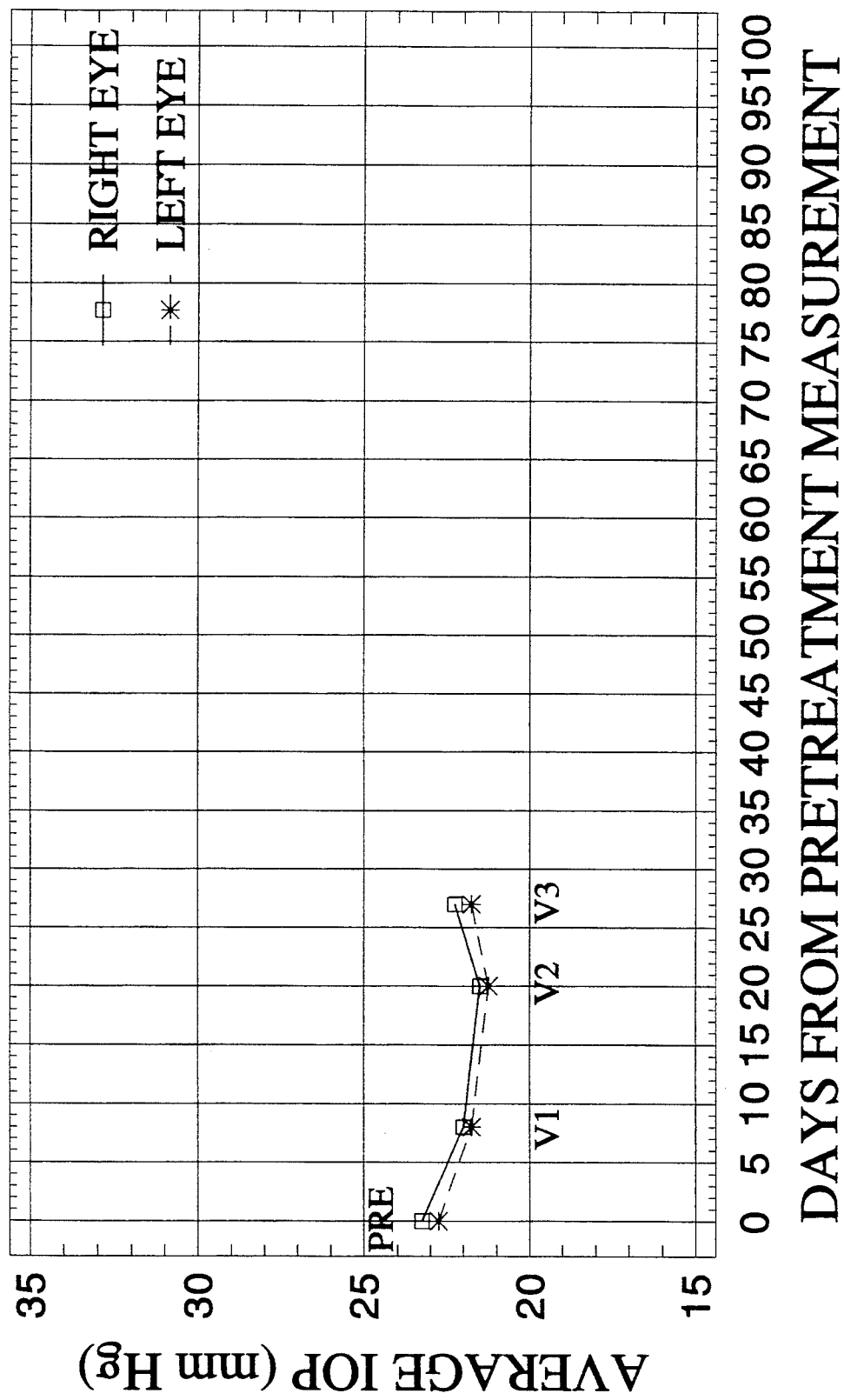
FIG. 12 is a graph showing the average intraocular pressures (IOP) plotted against days of treatment for the twelfth patient treated according to the inventive method.
Figure 17:
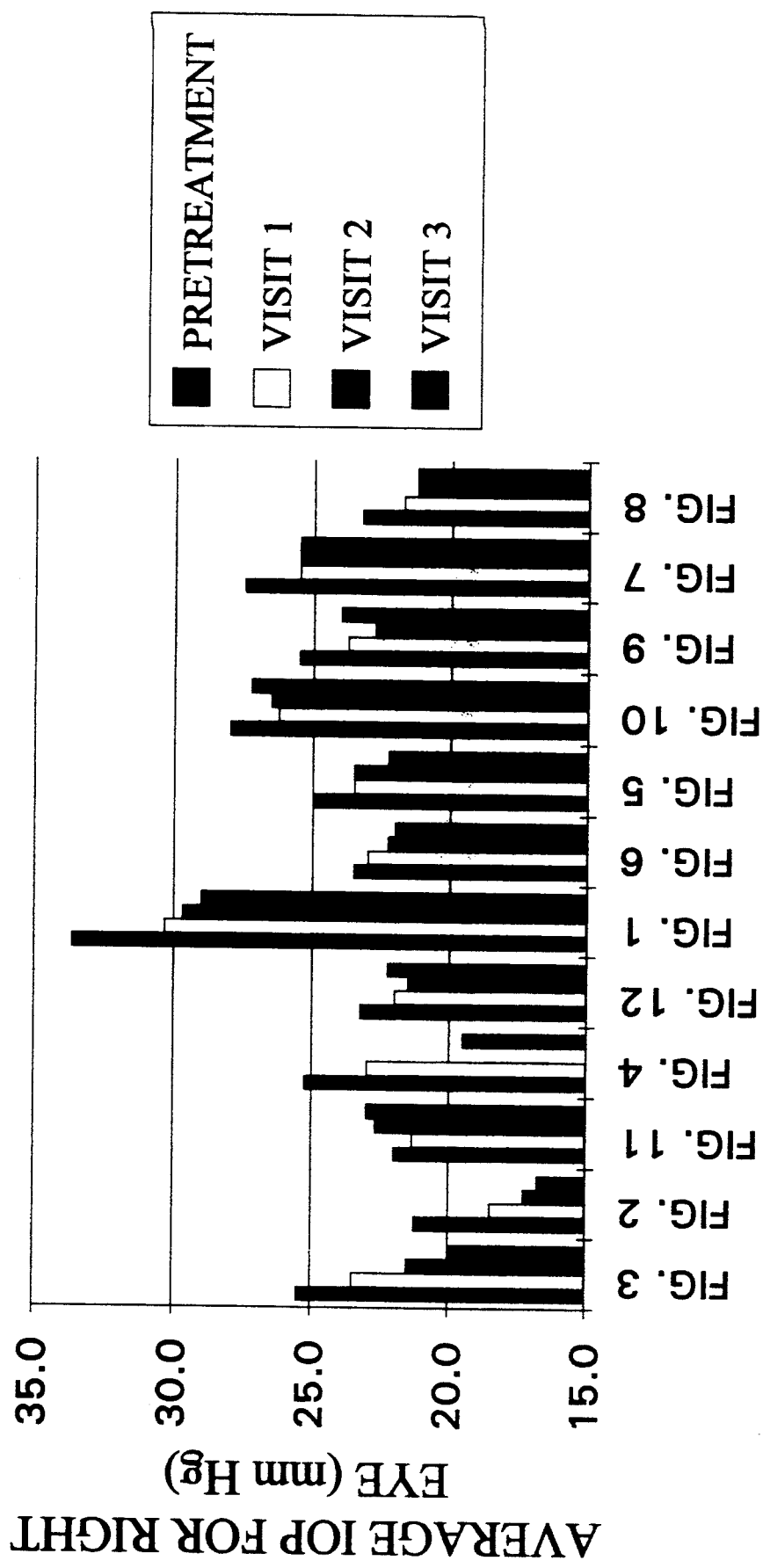
FIG. 17 is a bar graph showing the average IOP per visit for all subjects for the right eye.
Figure 18:
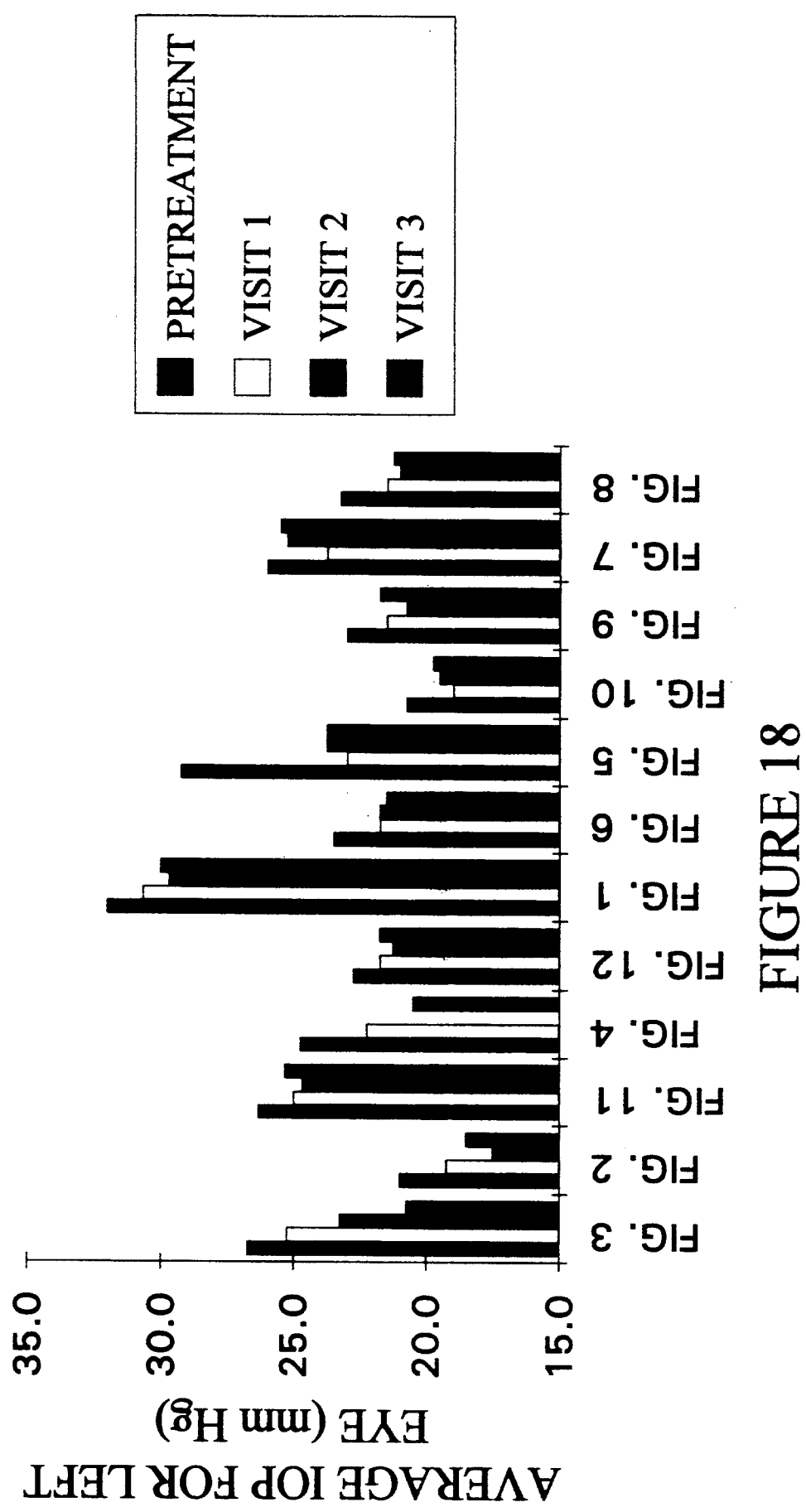
FIG. 18 is a bar graph showing the average IOP per visit for all subjects for the left eye.
Figure 19:
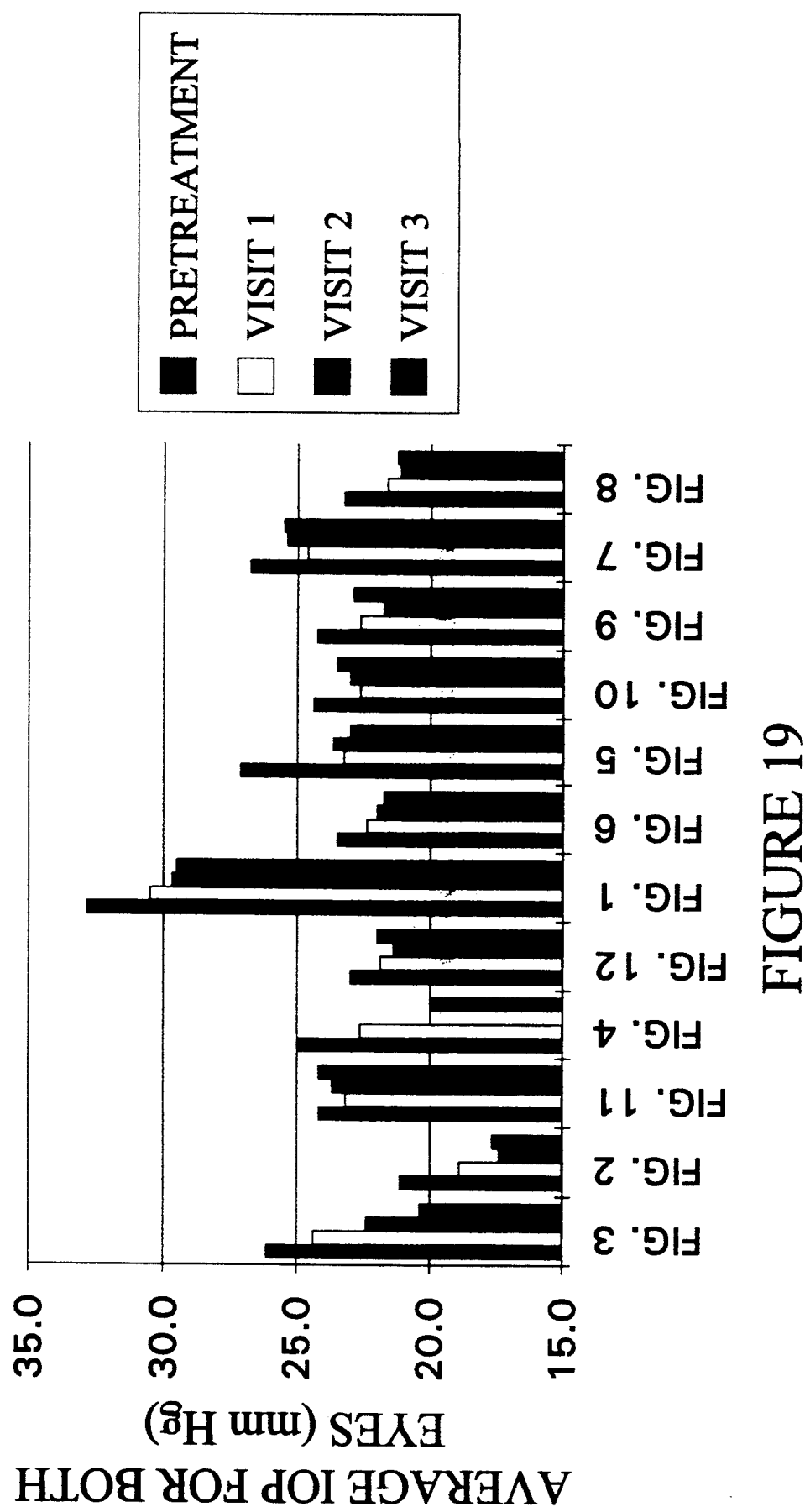
FIG. 19 is a bar graph showing the average IOP per visit for all subjects for both eyes.

The changes in average IOP for all hours for the PRE, V1, V2 and V3 visits for each of the 12 patients are presented for the right eye in FIG. 17 and for the left eye in FIG. 18. The changes in average IOP for all hours for the PRE, V1, V2 and V3 visits for each visit for both eyes are presented in FIG. 19. Based upon the apparent clinical response to ECA, the group is comprised of five clinically good responders (see FIGS. 1-5); four intermediate responders (see FIGS. 6-9); and three poor responders (see FIGS. 10-12).

Figure 5:
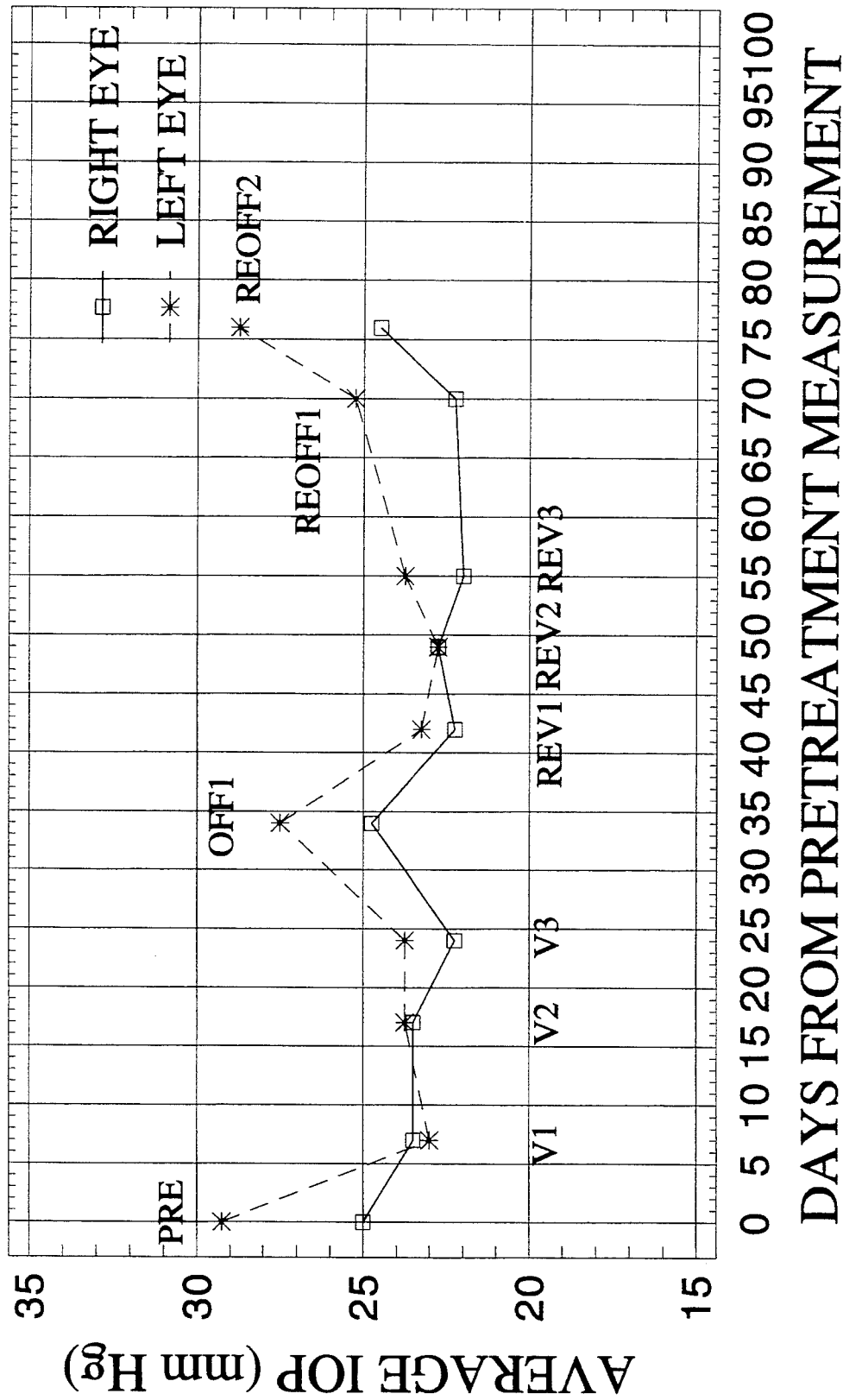
FIG. 5 is a graph showing the average intraocular pressures (IOP) plotted against days of treatment for the fifth patient treated according to the inventive method.

The pressure elevation response to discontinuation of ECA from visit 3 to OFF is presented in FIGS. 2-6 and 10 and Table 7 below. When all six patients represented by these figures are included, the difference between OFF and V3 is significant for the right eye with $P<0.05$. When the effect on IOP of discontinuation only in the four good responders (FIGS. 2-5) is analyzed, the difference between OFF and V3 is significant for both the right and left eyes with $P<0.01$. The plot of the pressure response of the patient depicted in FIG. 5 illustrates the reproducibility of the clinical response to ECA.

TABLE 7

Figure 6:
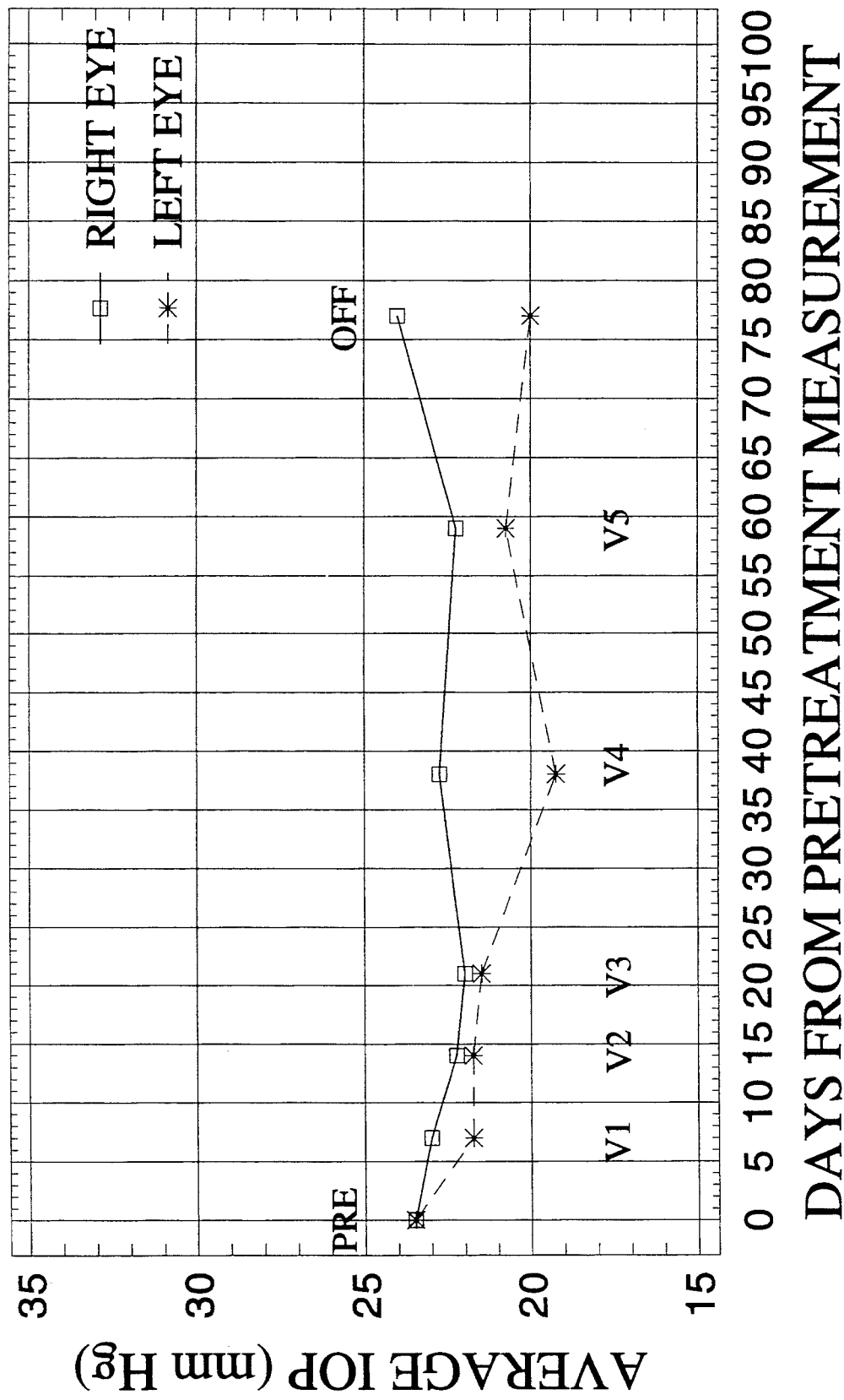
FIG. 6 is a graph showing the average intraocular pressures (IOP) plotted against days of treatment for the sixth patient treated according to the inventive method.
Figure 7:
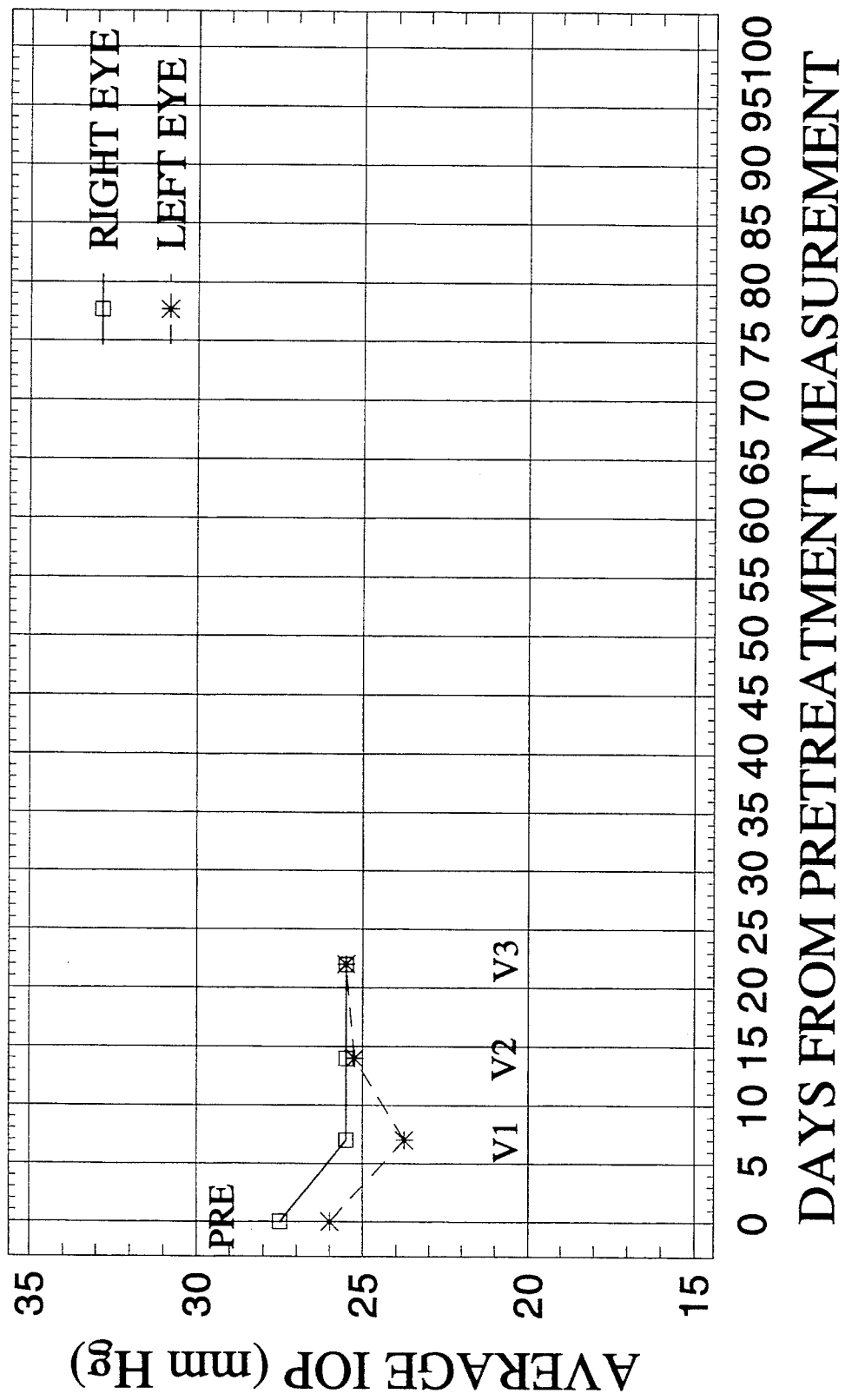
FIG. 7 is a graph showing the average intraocular pressures (IOP) plotted against days of treatment for the seventh patient treated according to the inventive method.
Figure 8:
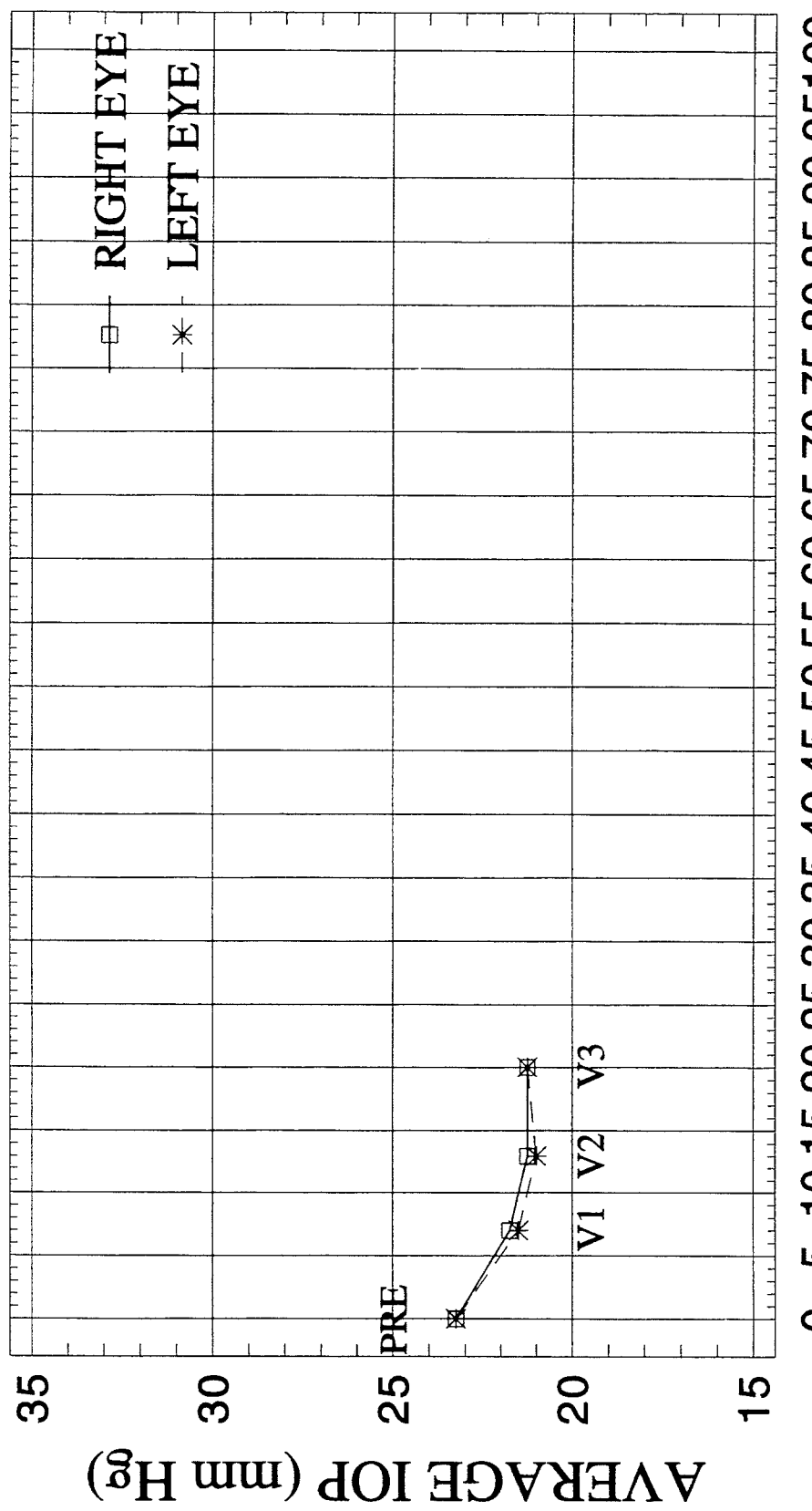
FIG. 8 is a graph showing the average intraocular pressures (IOP) plotted against days of treatment for the eighth patient treated according to the inventive method.
Figure 9:
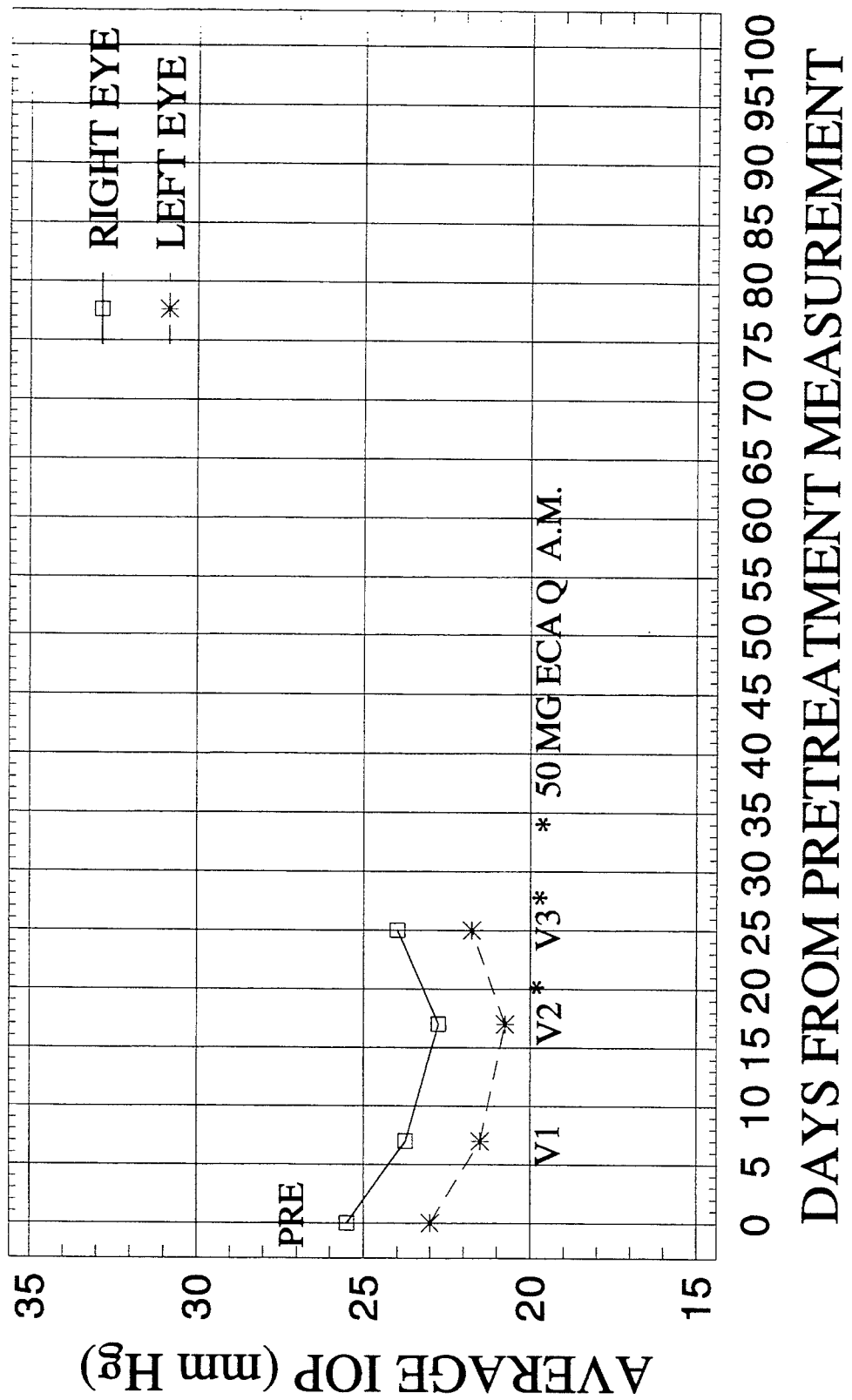
FIG. 9 is a graph showing the average intraocular pressures (IOP) plotted against days of treatment for the ninth patient treated according to the inventive method.
Figure 10:
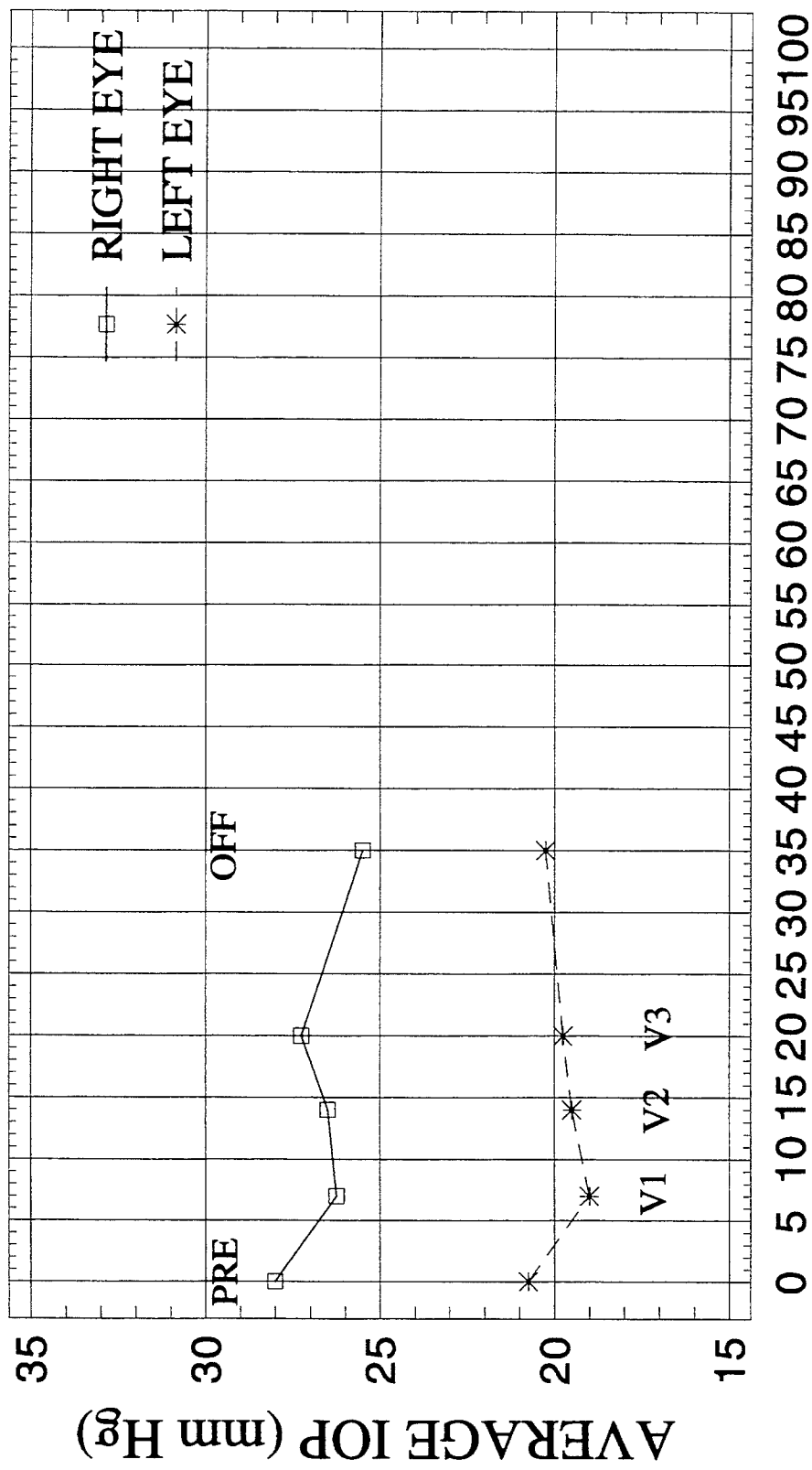
FIG. 10 is a graph showing the average intraocular pressures (IOP) plotted against days of treatment for the tenth patient treated according to the inventive method.

| | Obs | Aver | SD | Sig p ≦ |
|---|---|---|---|---|
| ELEVATION OF IOP FOLLOWING DISCONTINUATION OF ECA | | | | |
| Right Eye Average IOP all hours OFF-V3 | | | | |
| All | 6 | 2.75 | 2.53 | 0.0450 |
| FIGS. 6 & 10 | 4 | 4.06 | 1.21 | 0.0068 |
| Left Eye Average IOP all hours OFF-V3 | | | | |
| All | 6 | 2.54 | 2.61 | 0.0631 |
| FIGS. 6 & 10 | 4 | 4.06 | 1.21 | 0.0068 |
| Right Eye Average % change overflow pr V3 vs OFF | | | | |
| All | 6 | 30.83 | 26.22 | 0.0346 |
| FIGS. 6 & 10 | 4 | 44.62 | 16.30 | 0.0120 |
| Left Eye Average % change overflow pr V3 vs OFF | | | | |
| All | 6 | 23.83 | 23.88 | 0.0584 |
| FIGS. 6 & 10 | 4 | 37.72 | 11.12 | 0.0065 |

Electrolyte levels, as well as serum uric acid, glucose, and blood urea nitrogen were periodically monitored. Most of the patients levels remained within clinically acceptable ranges. One patient who had an elevated uric acid level (patient depicted in FIG. 3) was one of the better responders. This may suggest that there might be a correlation between increased uric acid and better response to treatment of the inventive method. None of the patients experienced any clinically significant changes in blood pressure. Some of the patients experienced some minor symptoms including gastrointestinal distress, lightheadedness, leg cramps and excessive urination.

As a result of the study, chronically administered ECA at a dosage of 50 mg bid was found to have a significant pharmacologic effect in reducing intraocular pressure in a heterogeneous group of open angle glaucoma patients. The present inventor found that one of the good responders was unsuccessful in attaining control of the intraocular pressure on most topical or oral glaucoma medication and was unresponsive to argon laser trabeculoplasty, thereby suggesting that the method of the present invention is more than an alternative to present treatments, but rather may be a necessary treatment for some patients.

The effect of chronic administration was manifest at one week, with a tendency to become greater over the next two weeks. The effect diminished within one to three weeks of cessation of treatment. It is also significant to note that, in the patient depicted in FIG. 5, at REOFF1, the IOP was significantly lower than the base line measurement, and at REOFF2 was still lower than the base line IOP measurement, thereby suggesting the possibility of a lasting therapeutic effect.

While preferred embodiments, forms and arrangements of parts of the invention have been described in detail, it will be apparent to those skilled in the art that the disclosed embodiments may be modified. Therefore, the foregoing description is to be considered exemplary rather than limiting, and the true scope of the invention is that defined in the following claims.

What is claimed is:

1. A method for treating glaucoma in an eye of a human patient, the method comprising the step of:
   chronically, orally administering to the patient an unsaturated ketone derivative of an aryloxyacetic acid in an amount sufficient to safely and effectively lower intraocular pressure in the human eye.

2. The method as defined in claim 1 wherein the unsaturated ketone derivative is selected from the group consisting of ethacrynic acid, an analog of ethacrynic acid, an ester derivative of ethacrynic acid, an ester derivative of an ethacrynic acid analog, an amide derivative of ethacrynic acid, an amide derivative of an ethacrynic acid analog, a pharmaceutically acceptable salt of ethacrynic acid, a pharmaceutically acceptable salt of an ethacrynic acid analog, a pharmaceutically acceptable salt of the ester derivative, a pharmaceutically acceptable salt of the amide derivative, and mixtures thereof.

3. The method as defined in claim 2 wherein the unsaturated ketone derivative is of the general formula:

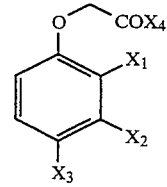

wherein each $X_1$ and $X_2$, independently, is a halogen, H, or $CH_3$, or $X_1$ and $X_2$ together form a substituted or unsubstituted aromatic ring; $X_3$ is an organic group; and $X_4$ is OH or an organic group.

4. The method as defined in claim 3 wherein each $X_1$ and $X_2$, independently, is H, Cl, or $CH_3$, or $X_1$ and $X_2$ together form a phenyl ring; $X_3$ is one of chloropropanyl, tosyl or mesyl; and $X_4$ is one of hydroxy, amino or alkoxy.

5. The method as defined in claim 3 wherein $X_3$ is a sulfhydryl reactive organic group.

6. The method as defined in claim 2 wherein the amount administered is between about 50 mg and about 75 mg two times per day.

7. The method as defined in claim 2 wherein the amount administered is between about 100 mg and about 150 mg daily.

8. A method for treating glaucoma in an eye of a human patient, the method comprising the step of:

chronically, orally administering ethacrynic acid to the patient in an amount sufficient to safely and effectively lower intraocular pressure in the human eye, wherein the amount administered is between about 50 mg and about 75 mg two times per day.

9. A method for lowering intraocular pressure in an eye of a human patient, the method comprising the step of:

chronically, orally administering to the patient an unsaturated ketone derivative of an aryloxyacetic acid in an amount sufficient to safely and effectively lower intraocular pressure in the human eye.

10. The method as defined in claim 9 wherein the unsaturated ketone derivative is selected from the group consisting of ethacrynic acid, an analog of ethacrynic acid, an ester derivative of ethacrynic acid, an ester derivative of an ethacrynic acid analog, an amide derivative of ethacrynic acid, an amide derivative of an ethacrynic acid analog, a pharmaceutically acceptable salt of ethacrynic acid, a pharmaceutically acceptable salt of an ethacrynic acid analog, a pharmaceutically acceptable salt of the ester derivative, a pharmaceutically acceptable salt of the amide derivative, and mixtures thereof.

11. The method as defined in claim 10 wherein the unsaturated ketone derivative is of the general formula:

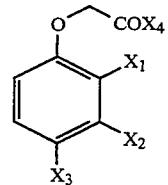

wherein each $X_1$ and $X_2$, independently, is a halogen, H, or $CH_3$, or $X_1$ and $X_2$ together form a substituted or unsubstituted aromatic ring; $X_3$ is an organic group; and $X_4$ is OH or an organic group.

12. The method as defined in claim 11 wherein each $X_1$ and $X_2$, independently, is H, Cl, or $CH_3$, or $X_1$ and $X_2$ together form a phenyl ring; $X_3$ is one of chloropropanyl, tosyl or mesyl; and $X_4$ is one of hydroxy, amino or alkoxy.

13. The method as defined in claim 11 wherein $X_3$ is a sulfhydryl reactive organic group.

14. The method as defined in claim 10 wherein the amount administered is between about 50 mg and about 75 mg two times per day.

15. The method as defined in claim 10 wherein the amount administered is between about 100 mg and about 150 mg daily.

16. The method as defined in claim 10 wherein the intraocular pressure is lowered for an indefinite amount of time after discontinuing oral administration of the unsaturated ketone derivative.

17. The method as defined in claim 10 wherein the oral administration of the unsaturated ketone derivative takes place concurrently with the administration of another intraocular pressure lowering treatment.

18. A method for lowering intraocular pressure in an eye of a human patient, the method comprising the step of:

chronically, orally administering ethacrynic acid to the patient in an amount sufficient to safely and effectively lower intraocular pressure in the human eye, wherein the amount administered is between about 50 mg and about 75 mg two times per day.

* * * * *